(12) United States Patent
Paul

(10) Patent No.: US 9,644,880 B2
(45) Date of Patent: May 9, 2017

(54) COOLING DEVICE

(71) Applicant: Mastaneh Paul, Pittsburgh, PA (US)

(72) Inventor: Mastaneh Paul, Pittsburgh, PA (US)

(73) Assignees: Rachel Kimia Paul, Pittsburgh, PA (US); Joshua Ari Paul, Pittsburgh, PA (US)

( * ) Notice: Subject to any disclaimer, the term of this patent is extended or adjusted under 35 U.S.C. 154(b) by 455 days.

(21) Appl. No.: 14/162,789

(22) Filed: Jan. 24, 2014

(65) Prior Publication Data

US 2014/0216061 A1   Aug. 7, 2014

Related U.S. Application Data

(60) Provisional application No. 61/756,024, filed on Jan. 24, 2013.

(51) Int. Cl.
*F24D 5/00* (2006.01)
*F25D 5/02* (2006.01)
*A61F 7/10* (2006.01)
*A41D 13/005* (2006.01)
*A61F 7/00* (2006.01)
*A61F 7/02* (2006.01)

(52) U.S. Cl.
CPC ............... *F25D 5/02* (2013.01); *A61F 7/106* (2013.01); *A41D 13/0053* (2013.01); *A61F 2007/0007* (2013.01); *A61F 2007/0011* (2013.01); *A61F 2007/0035* (2013.01); *A61F 2007/0228* (2013.01); *A61F 2007/0231* (2013.01); *A61F 2007/0276* (2013.01); *F25D 2400/26* (2013.01)

(58) Field of Classification Search
CPC ...... F25D 5/02; F25D 31/007; F25D 2400/26; A62B 17/005
USPC ...................................... 62/4, 259.3
See application file for complete search history.

(56) References Cited

U.S. PATENT DOCUMENTS

| | | |
|---|---|---|
| 2,250,840 A | 7/1941 | Pomeranz |
| 3,149,943 A | 9/1964 | Amador |
| 3,643,665 A | 2/1972 | Caillouette |
| 3,871,376 A | 3/1975 | Kozak |
| 4,397,315 A | 8/1983 | Patel |

(Continued)

FOREIGN PATENT DOCUMENTS

| | | |
|---|---|---|
| WO | 2013027066 A2 | 2/2013 |
| WO | 2014159422 A1 | 10/2014 |

*Primary Examiner* — Melvin Jones
(74) *Attorney, Agent, or Firm* — The Webb Law Firm

(57) ABSTRACT

A cooling device and methods of using the cooling device are described. The cooling device includes a flexible, elongated body member having a first end portion and a second end portion, or is adjustable with the first end portion and the second end portion attached, the elongated body member forming an elongated cavity extending substantially between the first end portion and the second end portion, the cavity having a first substance disposed within the cavity. The cooling device further includes at least one rupturable compartment contained within the cavity, the compartment having a second substance disposed within the compartment. The cooling device also includes fastening means disposed on at least one of the first end portion and the second end portion for detachably fastening the first end portion to the second end portion to secure the cooling device around a circumference of a body part.

21 Claims, 6 Drawing Sheets

(56) References Cited

U.S. PATENT DOCUMENTS

| | | |
|---|---|---|
| 4,575,097 A | 3/1986 | Brannigan et al. |
| 4,576,169 A | 3/1986 | Williams |
| 4,745,922 A | 5/1988 | Taylor |
| 4,832,030 A | 5/1989 | De Canto |
| 5,123,411 A * | 6/1992 | Noziri ............... A61F 7/106 604/113 |
| 5,305,470 A * | 4/1994 | McKay ............... A41D 20/005 2/170 |
| 5,431,622 A | 7/1995 | Pyrozyk et al. |
| 5,557,807 A | 9/1996 | Hujar et al. |
| 5,650,090 A | 7/1997 | Salyer |
| 5,887,437 A | 3/1999 | Maxim |
| 5,956,963 A | 9/1999 | Lerner |
| 6,183,501 B1 | 2/2001 | Latham |
| 6,233,945 B1 | 5/2001 | Kohout |
| 6,248,125 B1 | 6/2001 | Helming |
| 6,251,131 B1 | 6/2001 | Kohout |
| 6,393,843 B2 | 5/2002 | Kohout |
| 6,432,125 B2 | 8/2002 | Kohout |
| 6,648,909 B2 | 11/2003 | Helming |
| 6,666,834 B2 | 12/2003 | Restle et al. |
| 6,666,836 B1 | 12/2003 | Islava |
| 6,682,552 B2 | 1/2004 | Ramsden et al. |
| 6,893,455 B1 | 5/2005 | Rafferty et al. |
| 6,969,399 B2 | 11/2005 | Schock et al. |
| 7,096,687 B2 | 8/2006 | Trinh et al. |
| 7,197,893 B2 | 4/2007 | Trinh et al. |
| 7,739,748 B2 | 6/2010 | Nilforushan et al. |
| 2002/0103520 A1 | 8/2002 | Latham |
| 2005/0080368 A1 | 4/2005 | Hurwitz |
| 2006/0213156 A1 | 9/2006 | Nilfuroshan |
| 2007/0185555 A1 | 8/2007 | Partrich et al. |
| 2008/0209932 A1 | 9/2008 | Clarke et al. |
| 2008/0281307 A1 | 11/2008 | Donahue |
| 2009/0152296 A1 * | 6/2009 | May ............... B05C 17/00553 222/129 |
| 2009/0209893 A1 | 8/2009 | Sandhu |
| 2009/0276018 A1 | 11/2009 | Brader |
| 2014/0245527 A1 | 9/2014 | Douglas et al. |
| 2015/0253057 A1 | 9/2015 | Leavitt et al. |

* cited by examiner

COOLING DEVICE

BACKGROUND OF THE INVENTION

Field of the Invention

This invention relates to a device for cooling a portion of a person's body. More particularly, this invention relates to a cooling device which can be secured around a body part to absorb energy from the body upon initiating an endothermic reaction within a cavity of the device.

Description of Related Art

Overheating and body temperature fluctuations are common sources of discomfort. Such discomfort can arise as a result of, for example, exercising, illness, or certain medical conditions such as menopause, to name but a few. When one experiences such feelings, it is common to bring a cool surface into contact with the body. The cool surface can act to absorb energy from the body and provide an immediate sense of relief from the discomfort caused by overheating and body temperature fluctuations.

Devices that are useful for such purposes are known in the art. These devices are sometimes referred to as "cold packs." One type of cold pack is an instant cold pack, which uses an endothermic reaction that is initiated by mixing together chemical reagents contained in separate portions of the pack. Another type of cold pack is a reusable cold pack, which often contains a gel material that can be cooled and/or frozen by placing it in a refrigerator or freezer and then removed from the refrigerator or freezer for use. Conventional phase change systems also can be used as cold packs, the most common example of which would be water, which can change between a solid, when cold, and a liquid, when warm.

Attempts have been made to utilize existing cold pack technology for different applications. For instance, U.S. Pat. No. 6,251,131 to Kahout is directed to an absorbent ice bag that can be regenerated in situ. By way of another example, U.S. Pat. No. 6,666,836 to Islava is directed to a thermal dressing that can be used to attach a cold pack to a patient's body. By way of yet another example, U.S. Pat. No. 4,832,030 to De Canto is directed to a collar apparatus that retains a hot or cold pack insert.

Despite the efforts to date, the existing cool packs are often cumbersome to use, expensive to manufacture, and/or fail to stay securely in contact with a body part.

SUMMARY OF THE INVENTION

In one aspect, a cooling device is described. The cooling device comprises a flexible, elongated body member having a first end portion and a second end portion, the elongated body member forming an elongated cavity extending substantially between the first end portion and the second end portion, the cavity having a first substance disposed within the cavity. The cooling device further comprises at least one rupturable compartment contained within the cavity, the compartment having a second substance disposed within the compartment. The cooling device also comprises fastening means disposed on at least one of the first end portion and the second end portion for detachably fastening the first end portion to the second end portion to secure the cooling device around a circumference of a body part, or adjustably attached to secure the cooling device around a circumference of a body part, or disposed within an external accessory device that holds the cooling device and can be fastened around a circumference of a body part.

In some non-limiting embodiments, the cooling device is configured such that rupturing of the rupturable capsule causes the first substance to mix with the second substance within the cavity. In some non-limiting embodiments, mixing of the first substance and the second substance causes an endothermic reaction to occur. The temperature of the mixture of the first substance and the second substance is less than a temperature of the body part.

In some non-limiting embodiments, the fastening means is selected from a hook and loop fastener, a snap fastener, a single-sided adhesive material, a double-sided adhesive material, a tie wrap, a knot, an adjustable elastic means or attached to the body by means of an external accessory device that holds the cooling device to the body.

In some non-limiting embodiments, the first substance is ammonium nitrate or urea and the second substance is water. In other embodiments, the first substance is water and the second substance is ammonium nitrate or urea or another combination of substances that can trigger an endothermic reaction within the embodiment.

In some non-limiting embodiments, the elongated cavity is configured to wrap substantially around a person's neck when the first end portion is fastened to the second end portion, or adjustably attaches the first end portion and second end portion together. In other non-limiting embodiments, the elongated cavity is configured to wrap substantially around a person's head when the first end portion is fastened to the second end portion, or adjustably fastened to fit around a person's head. In still other non-limiting embodiments, the elongated cavity is configured to wrap substantially around a person's wrist when the first end portion is fastened to the second end portion, or adjustably fastened to fit around a person's wrist.

In some non-limiting embodiments, the body member is formed from a disposable material.

In another aspect, a method of cooling a body part is described. The method comprises placing a cooling device around a circumference of the body part. The cooling device comprises a flexible, elongated body member having a first end portion and a second end portion, the elongated body member forming an elongated cavity extending substantially between the first end portion and the second end portion, the cavity having a first substance disposed within the cavity; at least one rupturable compartment contained within the cavity, the compartment having a second substance disposed within the compartment; and fastening means disposed on at least one of the first end portion and the second end portion for detachably fastening the first end portion to the second end portion. The method further comprises fastening the first end portion of the cooling device to the second end portion of the cooling device to secure the cooling device around the circumference of the body part, or looping the cooling device around the circumference of the body part using an adjustable elastic body. In addition, the method comprises rupturing the rupturable compartment to cause the first substance to mix with the second substance within the cavity. Mixing of the first substance and the second substance causes an endothermic reaction to occur.

In some non-limiting embodiments, the rupturable compartment is ruptured before the cooling device is placed around the circumference of the body part. In other non-limiting embodiments, the rupturable compartment is ruptured after the cooling device is secured around the circumference of the body part.

In some non-limiting embodiments, the fastening means is selected from a hook and loop fastener, a snap fastener, a single-sided adhesive material, a double-sided adhesive material, a tie wrap, a knot, an adjustable elastic means or another means of fastening.

In some non-limiting embodiments, the first substance is ammonium nitrate or urea and the second substance is water. In other non-limiting embodiments, the first substance is water and the second substance is ammonium nitrate or urea. Or the first substance is water and the second substance is another combination of substances that can trigger an endothermic reaction within the embodiment.

In some non-limiting embodiments, the cooling device can be placed around the neck. In other non-limiting embodiments, the cooling device can be placed around the wrist. In still other non-limiting embodiments, the cooling device can be placed around the head.

In another aspect, another embodiment of a cooling device is described. The cooling device comprises a flexible, elongated body member having a first end portion and a second end portion, the elongated body member forming an elongated cavity extending substantially between the first end portion and the second end portion, the cavity having a first substance disposed within the cavity. The cooling device further comprises at least one rupturable compartment contained within the cavity, the compartment having a second substance disposed within the compartment. The cooling device also comprises fastening means disposed on at least one of the first end portion and the second end portion for detachably fastening the first end portion to the second end portion to secure the cooling device around a circumference of a body part, or having the first end portion adjustably attached to the second end portion. Rupturing of the rupturable compartment causes the second substance to be ejected from the compartment and mix with the first substance within the cavity and mixing of the first substance and the second substance causes an endothermic reaction to occur. In another embodiment the cooling device is disposed within an external accessory device in which the cooling element can be activated. This external accessory device is fastened to the body using a means of fastening such as a hook and loop fastener, a snap fastener, a spring fastener, a single-sided adhesive material, a double-sided adhesive material, a tie wrap, a knot, an adjustable elastic means or another means of fastening.

These and other aspects of the invention will be apparent from the description provided herein.

DETAILED DESCRIPTION OF THE INVENTION

Figure 1:
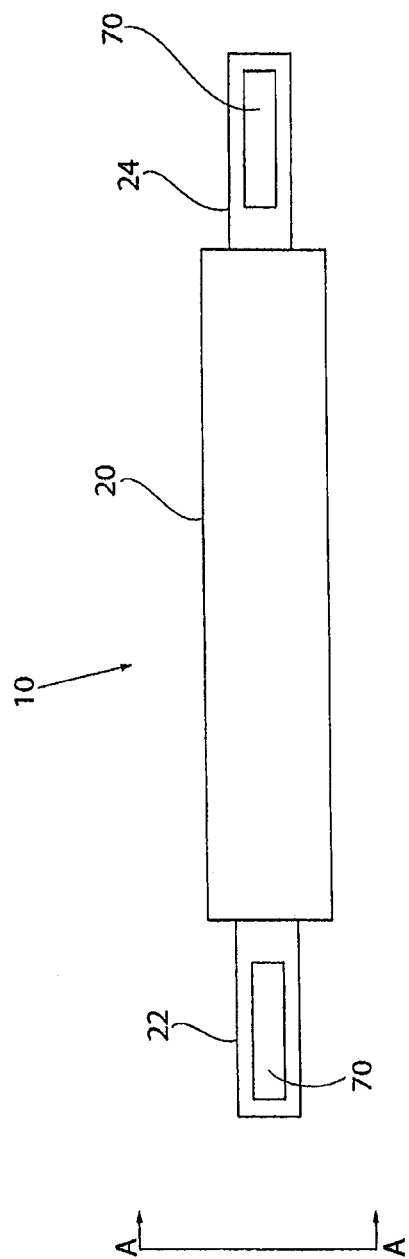
FIG. 1 is a perspective view showing one embodiment of the cooling device of the present invention.

As used herein, spatial or directional terms, such as "left," "right," "inner," "outer," "above," "below," "top," "bottom," and the like, relate to the device as it is shown in FIG. 1. However, it is to be understood that the device may assume various alternative orientations and, accordingly, such terms are not to be considered as limiting. Further, as used herein, all numbers expressing dimensions, physical characteristics, and the like, used in the specification and claims are to be understood as being modified in all instances by the term "about."

Disclosed is a device that can be used to cool a body part, such as a neck, wrist, or head. Also disclosed are methods of using a device as described herein in connection with cooling a body part. In certain aspects, the cooling device provided herein can be used in recreational applications, including before, during or after an athletic event such as running (e.g., a marathon), bicycling, golfing, playing tennis, and other events where body temperature may become elevated due to physical exertion and/or exposure to the sun, humidity, and other environmental factors. The cooling device provided herein may be designed to be lightweight, easy to store, and easy to transport, including in one's handbag or backpack. The cooling device can be stored or even worn while in an inactive state and then activated to provide a cooling effect once the user so desires. These and other non-limiting features and advantages will be appreciated by the below description.

Figure 2:
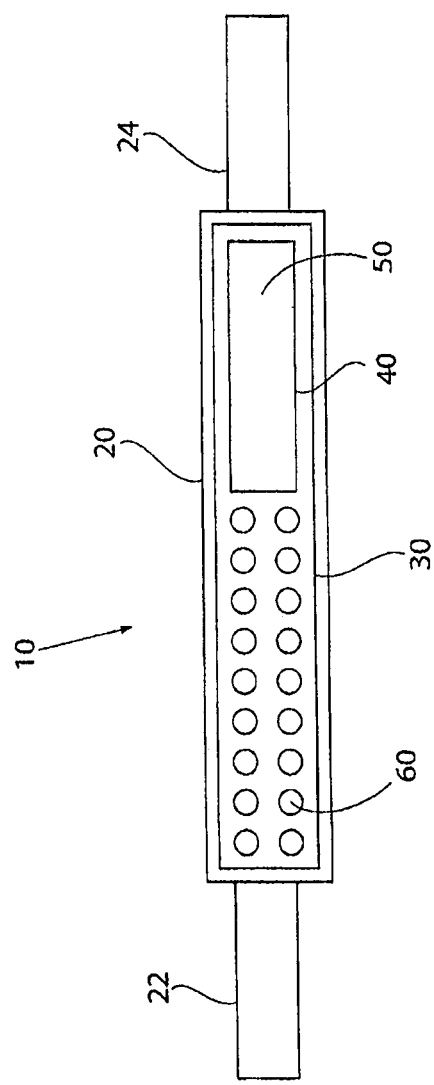
FIG. 2 is a cross-sectional view of the embodiment shown in FIG. 1 taken along line A-A.

Reference is now made to FIGS. 1 and 2, which shows one non-limiting embodiment of a cooling device 10 according to the present disclosure.

Cooling device 10 includes a flexible, elongated body member 20 which has a first end portion 22 and a second end portion 24. Elongated body member 20 forms an elongated cavity 30 which extends between the first end portion 22 and the second end portion 24. In some embodiments, elongated cavity 30 extends substantially between first end portion 22 and second end portions 24, and elongated cavity 30 can be contiguous with first end portion 22 and/or second end portion 24. The overall length and width of cooling device 10 and elongated body member 20 is dictated largely by the body part against which cooling device 10 is intended to be placed. If, for example, cooling device 10 is intended to be placed around the wrist, cooling device 10 should be at least 5, but preferably not more than 10 inches in length, so as to allow cooling device 10 to extend around the wrist. In such an embodiment, elongated cavity 30 should be sufficiently long such that it too extends around most, if not all, of the wrist surface, the reason for which will be apparent below. Cooling device 10 can also be between 1 and 3 inches wide in this embodiment. In another non-limiting embodiment, cooling device 10 can be intended to be placed around the neck. In such an embodiment, cooling device 10 can be at least 13 inches, but preferably not more than 20 inches in length, so as to allow cooling device 10 to extend completely around the neck. In such an embodiment, elongated cavity 30 should also be sufficiently long such that it too extends around most, if not all, of the neck surface. Cooling device can be between 1 and 3 inches as well. Other shapes and sizes of cooling device 10 are also envisioned.

Elongated body member 20 can be comprised of one or more layers of material. Non-limiting examples of materials that can be used in forming elongated body member 20 include polymers such as polyethylene and blends thereof, biodegradable polymers such as polylactic acid, and non-polymeric materials such as a woven or non-woven fabric material. Recyclable or biodegradable polymers have the advantage of providing less of an environmental impact when cooling member 10 is disposed of. All or a portion of elongated body member 20 can be impermeable to liquids.

For example, elongated body member 20 can be formed of a material that can isolate elongated cavity 30 from the surrounding environment, and thereby prevent liquids and/or gases from entering or exiting elongated cavity 30. In one embodiment, elongated body member 20 is formed of a single polymeric layer which forms an impermeable barrier between elongated cavity 30 and the surrounding environment. In another embodiment, elongated body member 30 is formed of two or more polymeric layers any of which may be laminated to one another. In still another embodiment, elongated body member 30 can be formed of one or more polymeric layers and an outer layer which is formed of a fabric material. An outer layer formed of a fabric material can provide cooling device 10 with a less abrasive outer surface, improving comfort when cooling device 10 is positioned against the skin. A fabric-based outer layer can also absorb perspiration that may be present on the skin and, additionally, can serve as an insulating layer. The fabric outer layer can be a sheath-like layer that is slid over all or a portion of elongated body member 20. The thickness of each layer of elongated body member 20, and the overall thickness of elongated body member 20, is not intended to be limited. However, elongated body member 20 should be sufficiently flexible to allow device 10 to be fitted around a body part such as a wrist, neck, or head. Further, elongated body member 20 should be sufficiently thin to allow thermal energy to quickly dissipate through elongated body member 20. In addition, one should also consider limiting the amount of material, and the cost of that material, used to form elongated body member 20 in order to minimize manufacturing costs, thereby making it economically feasible for cooling device 10 to be a one-time use product.

The outer layer of the elongated body member 30 or external accessory device 100 can have one or more designs and/or lettering printed or embossed on the exterior thereof. The design(s) and or lettering can be indicative of source of the product, advertising for a company or event, slogans, etc. as desired.

Cooling device 10 further includes at least one rupturable compartment 50 that is contained within elongated cavity 30. Rupturable compartment 50 can be a self-contained packet or capsule fully contained within elongated cavity 30. Rupturable compartment 50 can include a shell which defines an inner area which is isolated from elongated cavity 30. The shell of rupturable compartment 50 can be composed of a polymeric or non-polymeric material, including those discussed above. For example, rupturable compartment 50 can be composed of a thin film of polypropylene. Rupturable compartment 50 can be connected to an inner surface of elongated body member 20 or otherwise held in place within elongated cavity 30, or rupturable compartment 50 can be free to move within some portion of elongated cavity 30 or throughout the entire length of elongated cavity 30. One or more portions of the shell which defines rupturable compartment 50 can also be a portion of elongated body member 30. For instance, rupturable compartment 50 and elongated body member 30 can share at least one surface. In one non-limiting embodiment, rupturable compartment 50 is defined by one or more layers of material extending across elongated cavity 30 in the radial direction to partition off a section of elongated cavity 30, with the area within said partition defining the rupturable compartment 50.

At least some portion of the shell of rupturable compartment 50 should be susceptible to being ruptured when subjected to a mild amount of pressure, such as the pressure that can be supplied by squeezing one's hand. By way of example, this can be accomplished by forming a portion of the shell of rupturable compartment 50 of a thin material. This could also be achieved by compromising at least a portion of the shell of rupturable compartment 50, such as by scoring, to make rupturable compartment 50 more easily ruptured. Once ruptured, the interior of rupturable compartment 50 and the elongated cavity 30 should be in fluid communication.

Cooling device 10 also includes a first substance 40 contained within elongated cavity 30 and a second substance 60 contained within rupturable compartment 50. Prior to use, first substance 40 and second substance 60 are isolated from one another by an impermeable barrier, which may be the shell of rupturable compartment 50. First substance 40 and second substance 60 are not limited, provided that, when first substance 40 and second substance 60 are brought into contact with one another, an endothermic reaction occurs. Examples of materials that can be used to effect an endothermic reaction are ammonium nitrate, urea and water. In one non-limiting embodiment, first substance 40 is ammonium nitrate or urea and second substance 60 is water. In another non-limiting embodiment, first substance 40 is water and second substance 60 is ammonium nitrate or urea. First substance 40 and/or second substance 60 can be comprised of a mixture of components as well. For example, first substance 40 may include ammonium nitrate or urea, and sodium acetate trihydrate while second substance 60 may include an aqueous solution of ethylene glycol. Other additives or coloring agents can be added to first substance 40 and/or second substance 60 as well.

When first substance 40 and second substance 60 are brought into contact with one another, such as by rupturing rupturable compartment 50, an endothermic reaction is initiated within elongated cavity 30, and this cooling effect is transferred through elongated body member 20, thus creating a cold surface on the outside of cooling device 10. If cooling device 10 is then placed on a body part, heat from the body part is absorbed, thus cooling the body part.

The amount of first substance 40 and second substance 60 used is not intended to be limited. However, because the amount of each, along with the identity of each, largely dictates the length and intensity of the endothermic reaction, the selection should take into account the desired length of the cooling effect. In some non-limiting embodiments, first and second substances 40, 60 are provided in amounts that allow for the surface of cooling device 10 to achieve a temperature of at or below 40° F. for between about 3 and 40 minutes, such as between about 10 and 30 minutes, or approximately 15 minutes. If a short cooling effect is desired, less of first and second substances 40, 60 can be used, lessening the cost and weight of cooling device 10. In addition, using less of first and second substances 40, 60 allows cooling device 10 to take on a thinner profile. The size of elongated cavity 30 should also be selected such that the first and second substances 40, 60, when mixed, provide a cool surface substantially along the entire length and width of elongated cavity 30.

Cooling device 10 also includes fastening means 70. Fastening means 70 are disposed on at least one of, and possibly both of, first end portion 22 and second end portion 24. Fastening means 70 is configured to allow first end portion 22 to be detachably connected to second end portion 24, or adjustably attached to secure the cooling device 10 around a circumference of a body part, or adjustably fastened, disposed or inserted within an external accessory device 100 (shown in FIG. 6) that holds the cooling device 10 and can be fastened around a circumference of a body part. Connecting first end portion 22 to second end portion 24 in this manner forms cooling device 10 into a loop and allows cooling device 10 to be secured around the circumference of, for example, a body part such as a wrist, head, or neck.

Fastening means 70 can be in the form of any conventional fastening mechanism known in the art. Non-limiting examples include hook and loop fasteners (e.g., VELCRO®), adhesive materials, snap and button fasteners, a tie wrap or an external accessory device holding the cooling element. By way of further explanation, and not intending to limit the fastening means 70, first end portion 22 can contain on a top surface hook fasteners while an underside of second end portion 24 can contain loop fasteners. The hook fasteners can then be brought into contact with the loop fasteners to secure first end portion 22 to second end portion 24. By way of another example, first end portion 22 can contain an adhesive material that can adhere to second end portion 24 when pressure is applied to the adhesive material to secure first end portion 22 to second end portion 24. In some non-limiting embodiments, the adhesive material can be a double-sided adhesive film that allows the top surface of first end portion 22 to be secured to the underside of second end portion 24. In other non-limiting embodiments, adhesive material can be a single-sided adhesive film, such as conventional packaging tape, which can bridge between the top surface of first end portion 22 and the top surface of second end portion 24. If an adhesive material is used, the adhesive material can have a removable cover layer that is removed prior to use in order to prevent the adhesive material from inadvertently adhering to another surface prior to use. By way of another example, first end portion 22 can include an aperture and second end portion 24 can include a tie material, which could be a string or thin metal strip (similar to the tie used with bread packaging), that can be threaded through aperture in order to secure first end portion 22 to second end portion 24 in a tie-wrap arrangement. Alternatively, apertures can be provided at each of first end portion 22 and second end portion 24, and a tie material could be threaded through the apertures once they are aligned with one another to secure first end portion 22 to second end portion 24. In another non-limiting embodiment, the male half of a snap fastener could be disposed on the top surface of first end portion 22 and the female half of a snap fastener could be disposed on the underside of second end portion 24. In yet another embodiment, first end portion 22 could include a button while second end portion 24 has a slit which can mate with the button.

Another means of fastening may include an external accessory that consists of elastic material or other adjustable closures that contains the cooling element and which band length is adjustable to fit various usage (neck, wrist or other body part) to allow for quick placement of the cooling element on the body.

Figure 6:
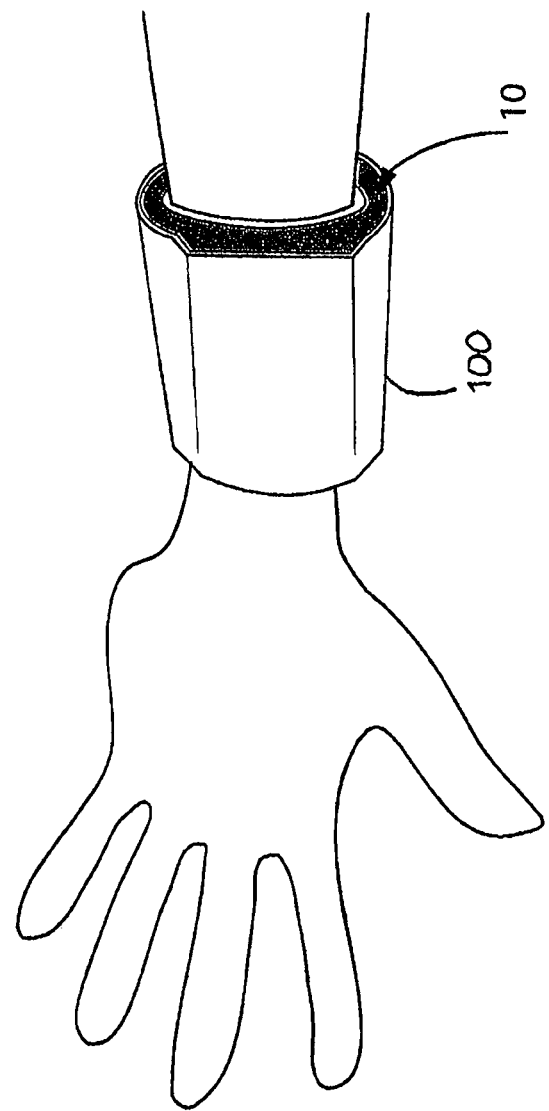
FIG. 6 is a perspective view showing the embodiment of the cooling device of FIG. 1 disposed within an external accessory device holding the cooling element and fastened around the user's wrist.

Referring now to FIG. 6, in some non-limiting embodiments, the fastening means 70 is an external accessory device 100 that holds the cooling device 10 and can be fastened around a circumference of a body part, for example a cuff. The cuff can be formed from a natural or synthetic material or a polymeric material. The cuff can be flexible to permit the rupturable compartment to be ruptured in situ. Alternatively, the cuff can be semi-rigid and the rupturable compartment can be ruptured before the cooling device is inserted into the external accessory device 100.

Also provided are methods of using cooling device 10 to cool and/or otherwise regulate the temperature of a body part. Cooling device 10 can be used in any situation where one desires to regulate his or her body temperature. Such situations can include during or after exercising, during or after surgery or another medical procedure, while suffering from an illness such as the flu, while subject to a hot environmental temperature, or while experiencing symptoms of a medical condition such as menopause where one experiences warmth that spreads over the body (e.g., "hot flashes").

Use of cooling device 10 involves rupturing the rupturable compartment 50 to allow first substance 40 and second substance 60 to come into contact with one another in order to initiate an endothermic reaction. Rupturing the rupturable compartment 50 involves applying pressure to rupturable compartment to rupture the barrier between rupturable compartment 50 and elongated cavity 30. The pressure required can be applied by gripping rupturable compartment 50 or a portion thereof in one's hand and squeezing one's hand together. Other non-limiting ways of rupturing rupturable compartment 50 include pressing rupturable compartment 50 against a surface, including the body, or placing rupturable compartment 50 between one's hands and squeezing one's hands together.

Cooling device 10 can be placed against the body, such as at the neck, wrist, or head in order to allow cooling device 10 to absorb heat from the body, creating a cooling effect on the body. Cooling device 10 can be placed directly against the body or cooling device 10 can be placed indirectly against the body, such as where an article of clothing, bandage, or other intermediate layer is between the outer surface of cooling device 10 and the body. In some non-limiting embodiments, use of cooling device 10 involves first rupturing the rupturable compartment 50 and then placing cooling device against the body. In other non-limiting embodiments, device 10 is first placed against the body and then rupturable compartment 50 is ruptured. In some non-limiting embodiments, cooling device 10 can be placed around the circumference of a body part such as the head, wrist, or neck. This can provide a cooling effect around most or even the entire body part, thus increasing the sensation associated with the use of cooling device 10.

Figure 3:
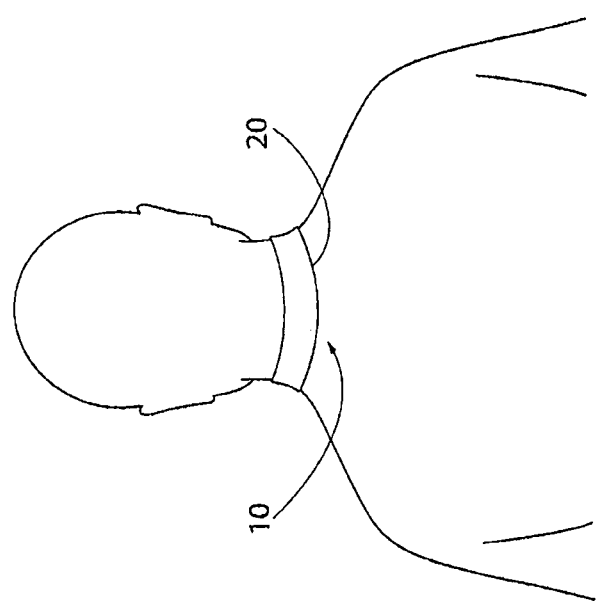
FIG. 3 is a perspective view showing the embodiment of FIG. 1 secured around a user's neck.
Figure 4:
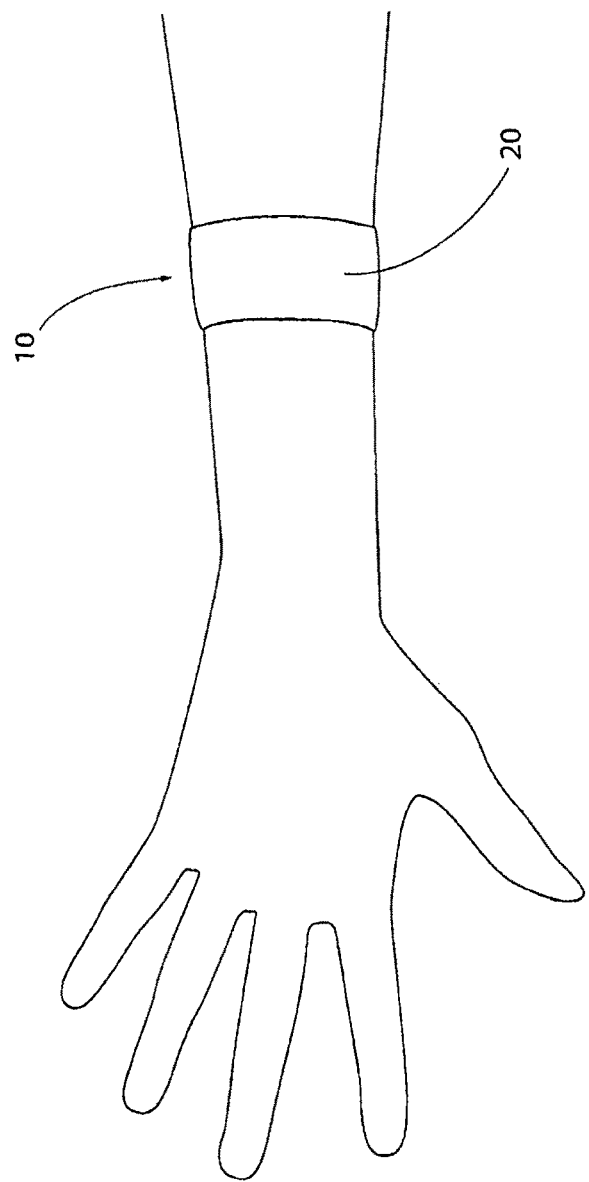
FIG. 4 is a perspective view showing the embodiment of FIG. 1 secured around a user's wrist.
Figure 5:
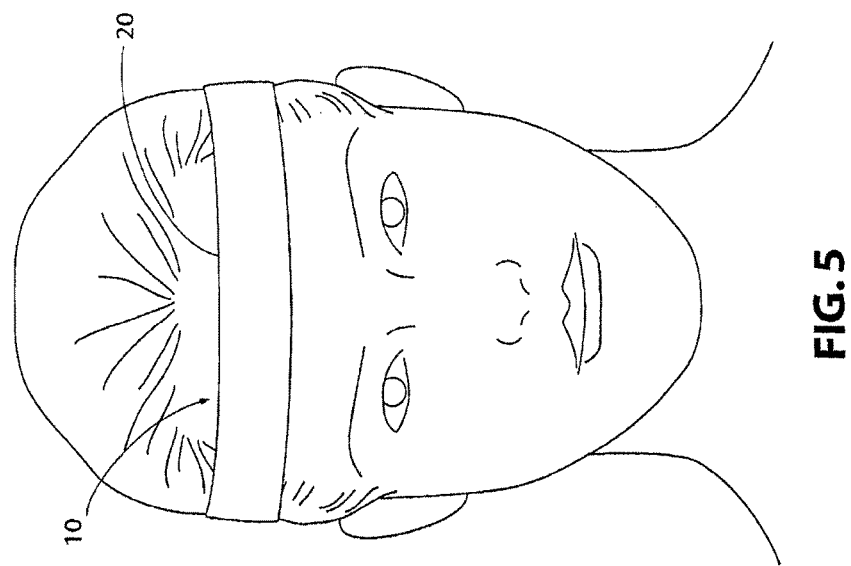
FIG. 5 is a perspective view showing the embodiment of FIG. 1 secured around a user's head.

Cooling device 10 can also be secured in place using fastening means 70. For example, cooling device 10 can be placed against the body and then secured in place by using fastening means 70. In some non-limiting embodiments, cooling device 10 can be placed around the neck, head, or wrist and then fastening means 70 can be used to secure cooling device 10 in this configuration. FIGS. 3, 4, and 5 show configurations of cooling device 10 secured around a neck, wrist, and head, respectively. Cooling device 10 can be secured against the body either before or after rupturing rupturable compartment 50 to initiate the endothermic reaction. Once secured, one can go about his or her activities without having to continue holding cooling device 10 in place, freeing up one's hands for other tasks. Cooling device 10 can also be worn underneath articles of clothing, such as under one's shirt sleeves or under one's collar, to conceal cooling device 10 from view.

Once finished with cooling device 10, either because the endothermic reaction has completed or because no additional cooling therapy is desired, cooling device 10 can be removed from the body and discarded or otherwise disposed of. In some non-limiting embodiments, the construction of cooling device 10 and selection of the materials of construction allow cooling device 10 to be intended for one-time use only. For example, cost effective materials can be used to construct cooling device 10 so that cooling device 10 remains economically viable as a one-time use product. In addition, selection of first substance 40 and second substance 60 may lend itself to a one-time use product when the endothermic reaction that is initiated by the mixing of first substance 40 and second substance 60 is either irreversible or not easily reversible such as in the case where ammonium nitrate and water are used. Cooling device 10 can also be constructed of recyclable materials and, following use of cooling device 10, it can be recycled.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

What is claimed is:

1. A cooling device, comprising:
a flexible, elongated body member having a first end portion and a second end portion, the elongated body member forming an elongated cavity extending substantially between the first end portion and the second end portion, the cavity having a first substance disposed within the cavity;
at least one rupturable compartment contained within the cavity, the compartment having a second substance disposed within the compartment; and
fastening means disposed on at least one of the first end portion and the second end portion for detachably fastening the first end portion to the second end portion to secure the cooling device around a circumference of a body part, or adjustably attached to secure the cooling device around a circumference of a body part, or disposed within an external accessory device that holds the cooling device and can be fastened around a circumference of a body part, wherein the first substance is ammonium nitrate or urea and the second substance is water.

2. A cooling device, comprising:
a flexible, elongated body member having a first end portion and a second end portion, the elongated body member forming an elongated cavity extending substantially between the first end portion and the second end portion, the cavity having a first substance disposed within the cavity;
at least one rupturable compartment contained within the cavity, the compartment having a second substance disposed within the compartment; and
fastening means disposed on at least one of the first end portion and the second end portion for detachably fastening the first end portion to the second end portion to secure the cooling device around a circumference of a body part, or adjustably attached to secure the cooling device around a circumference of a body part, or disposed within an external accessory device that holds the cooling device and can be fastened around a circumference of a body part, wherein the first substance is water and the second substance is ammonium nitrate or urea.

3. A method of cooling a body part, comprising:
placing a cooling device around a circumference of the body part, wherein the cooling device comprises:
a flexible, elongated body member having a first end portion and a second end portion, or having an adjustable elastic looped body, the elongated body member forming an elongated cavity extending substantially between the first end portion and the second end portion, the cavity having a first substance disposed within the cavity;
at least one rupturable compartment contained within the cavity, the compartment having a second substance disposed within the compartment; and
fastening means disposed of at least one of the first end portion and the second end portion for detachably fastening the first end portion to the second end portion;
fastening the first end portion of the cooling device to the second end portion of the cooling device, or looping the cooling device around a circumference of a body part using an adjustable elastic body; and
rupturing the rupturable compartment to cause the first substance to mix with the second substance within the cavity,
wherein mixing of the first substance and the second substance causes an endothermic reaction to occur.

4. The method of claim 3, wherein the rupturable compartment is ruptured before the cooling device is placed around the circumference of the body part.

5. The method of claim 3, wherein the rupturable compartment is ruptured after the cooling device is secured around the circumference of the body part.

6. The method of claim 3, wherein the fastening means is selected from the group consisting of: a hook and loop fastener, a snap fastener, a single-sided adhesive material, a double-sided adhesive material, and a tie wrap, a knot, adjustably fastened or inserted in an external accessory that is holding the cooling element onto the body.

7. The method of claim 3, wherein the first substance is ammonium nitrate or urea and the second substance is water.

8. The method of claim 3, wherein the first substance is water and the second substance is ammonium nitrate or urea.

9. The method of claim 3, wherein the body part is a neck.

10. The method of claim 3, wherein the body part is a wrist.

11. The method of claim 3, wherein the body part is a head.

12. A cooling device, comprising:
a flexible, elongated body member having a first end portion and a second end portion (either with the ends adjustably attached or unattached), the elongated body member forming an elongated cavity extending substantially between the first end portion and the second end portion, the cavity having a first substance disposed within the cavity;
at least one rupturable compartment contained within the cavity, the compartment having a second substance disposed within the compartment; and
fastening means disposed on at least one of the first end portion and the second end portion for detachably fastening the first end portion to the second end portion to secure the cooling device around a circumference of a body part, or having the first end portion adjustably attached to the second end portion,
wherein rupturing of the rupturable compartment causes the second substance to be ejected from the compartment and mix with the first substance within the cavity, and
wherein mixing of the first substance and the second substance causes an endothermic reaction to occur.

13. The cooling device of claim 1, wherein rupturing of the rupturable compartment causes the first substance to mix with the second substance within the cavity, wherein mixing of the first substance and the second substance causes an endothermic reaction to occur, and wherein a temperature of the mixture of the first substance and the second substance is less than a temperature of the body part.

14. The cooling device of claim 1, wherein the fastening means is selected from the group consisting of: a hook and loop fastener, a snap fastener, a single-sided adhesive material, a double-sided adhesive material, a tie wrap, a knot, an adjustable elastic means, and an external accessory device that can be fastened to the user's body and holds the cooling device.

15. The cooling device of claim 1, wherein the elongated cavity is configured to wrap substantially around a person's neck, a person's head, or a person's wrist when the first end portion is fastened to the second end portion or adjustably attaches the first end and second end portion together.

16. The cooling device of claim 1, wherein the body member is comprised of a disposable material.

17. The cooling device of claim 2, wherein rupturing of the rupturable compartment causes the first substance to mix with the second substance within the cavity, wherein mixing of the first substance and the second substance causes an endothermic reaction to occur, and wherein a temperature of the mixture of the first substance and the second substance is less than a temperature of the body part.

18. The cooling device of claim 2, wherein the fastening means is selected from the group consisting of: a hook and loop fastener, a snap fastener, a single-sided adhesive material, a double-sided adhesive material, a tie wrap, a knot, an adjustable elastic means, and an external accessory device that can be fastened to the user's body and holds the cooling device.

19. The cooling device of claim 2, wherein the elongated cavity is configured to wrap substantially around a person's neck, a person's head, or a person's wrist when the first end portion is fastened to the second end portion or adjustably attaches the first end and second end portion together.

20. The cooling device of claim 2, wherein the body member is comprised of a disposable material.

21. The cooling device of claim 12, wherein the body member is comprised of a disposable material.

* * * * *

UNITED STATES PATENT AND TRADEMARK OFFICE
CERTIFICATE OF CORRECTION

PATENT NO. : 9,644,880 B2  
APPLICATION NO. : 14/162789  
DATED : May 9, 2017  
INVENTOR(S) : Mastaneh Paul Page 1 of 1

It is certified that error appears in the above-identified patent and that said Letters Patent is hereby corrected as shown below:

In the Claims

Column 10, Line 8, Claim 3, delete "of at least" and insert -- on at least --

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*